United States Patent [19]  [11] 4,033,999
Onoda et al.  [45] July 5, 1977

[54] PROCESS FOR PREPARING A CARBOXYLIC ESTER

[75] Inventors: Takeru Onoda; Keisuke Wada, both of Yokohama, Japan

[73] Assignee: Mitsubishi Chemical Industries Ltd., Tokyo, Japan

[22] Filed: May 5, 1976

[21] Appl. No.: 683,529

Related U.S. Application Data

[63] Continuation-in-part of Ser. No. 548,779, Feb. 10, 1975, abandoned.

[30] Foreign Application Priority Data

Feb. 12, 1974 Japan .............................. 49-16922

[52] U.S. Cl. .................. 260/488 CD; 252/430; 260/479 R; 260/599
[51] Int. Cl.² .......................................... C07C 67/05
[58] Field of Search ................. 260/488 CD, 497 A

[56] References Cited

UNITED STATES PATENTS 3,274,238  9/1966  Kojer et al. ................... 260/497 A
3,755,423  8/1973  Onoda et al. ................. 260/497 A

FOREIGN PATENTS OR APPLICATIONS 1,017,938  1/1966  United Kingdom ......... 260/488 CD Primary Examiner—Vivian Garner
Attorney, Agent, or Firm—Oblon, Fisher, Spivak, McClelland & Maier

[57] ABSTRACT

A carboxylic ester of a substituted benzene compound having one or two hydroxymethyl groups on the benzene ring is prepared by reacting a benzene compound selected from the group consisting of toluene and xylene, an aliphatic carboxylic acid, and molecular oxygen in the gaseous phase, in the presence of a catalyst, wherein the improvement comprises reacting said reactants over a supported catalyst wherein the active constituents comprise (1) palladium, (2) an antimony component substantially as the oxide thereof and (3) at least one carboxylic acid salt of an alkali metal, alkaline earth metal, zinc, cadmium or lead, on a carrier.

14 Claims, No Drawings

4,033,999

PROCESS FOR PREPARING A CARBOXYLIC ESTER

The present application is a continuation-in-part of application Ser. No. 548,779, filed Feb. 10, 1975, now abandoned.

BACKGROUND OF THE INVENTION

1. Field of the Invention

The present invention relates to a process for preparing a carboxylic ester of an aromatic compound having a hydroxymethyl group on the aromatic ring by reacting an aromatic compound having a methyl group on the ring, an aliphatic carboxylic acid, and molecular oxygen.

2. Description of Prior Art

It has been know that noble metals of Group VIII of the Periodic Table, especially palladium, are effective as catalysts for the reaction described above (Japanese Patent Publication No. 13081/1967). It also has been known to add auxiliary catalysts, such as bismuth compounds, gold compounds, tin salts, organic phosphorus compounds or iron salts, etc. in order to enhance the catalytic activity. (Japanese Patent Application Publication No. 18843/1972 and U.S. Pat. No. 3,547,982). In the present case, a carboxylic acid salt of a metal of Groups IA or IIA of the Periodic Table can be added as an auxiliary activator. However, from the viewpoint of catalytic activity, some of these catalysts have been found to be unsatisfactory for industrial purposes. They suffer from disadvantages including the following. In order to increase the activity of palladium as a catalyst, high quality palladium has been employed, thereby substantially increasing cost. In the gaseous reactions, a decrease of the catalytic activity of the catalyst arises, in many instances within a short period of time. Moreover, in the conventional technology for this reaction, carboxylic esters of aromatic compounds having a hydroxyl group on the aromatic ring have been produced as a substantial side-product; in fact, so substantial that it often is the main product. Consequently, it would be desirable to have an inexpensive catalyst with a long lifetime which does not allow the formation of the aforementioned by-products.

CROSS-REFERENCE TO RELATED APPLICATIONS

The present inventors have filed a Patent Application, Ser. No. 475,984, filed June 3, 1974, now U.S. Pat. No. 3,959,354, in which a process is claimed for preparing a phenyl ester and/or phenol by reacting benzene, a carboxylic acid, and molecular oxygen in the presence of a catalyst which is similar to the catalyst used in the present invention.

SUMMARY OF THE INVENTION

Accordingly, it is one object of the present invention to provide a process for preparing a carboxylic ester of a substituted benzene compound having one or two hydroxymethyl groups by reacting a benzene compound selected from the group consisting of toluene and xylene, an aliphatic carboxylic acid, and molecular oxygen, using a catalyst which is characterized by high catalytic activity, high selectivity and long catalytic life.

This and other objects of this invention, as will hereinafter be made clear by the discussion below, has been attained by preparing a carboxylic ester of a substituted benzene compound having one or two hydroxymethyl groups on the benzene ring by reacting a benzene compound selected from the group consisting of toluene and xylene, an aliphatic carboxylic acid, and molecular oxygen in the gaseous phase, in the presence of a supported catalyst of palladium, an antimony component substantially as the oxide thereof, and at least one member of the groups of carboxylic acid salts wherein the metal is an alkali metal, an alkaline earth metal, zinc, cadmium or lead.

DETAILED DESCRIPTION OF THE PREFERRED EMBODIMENTS

The catalyst used for this invention consists essentially of three components which are supported on a carrier. Suitable carriers include silica, silica-alumina, alumina, active carbon, clay, bauxite, magnesia, diatomaceous earth, pumice, zeolite, titania, or the like. The first component of the catalyst is palladium metal. The particular palladium compound which can be used for the preparation of the catalyst of this invention is not critical. Preferred compounds include the halides, e.g., palladium chloride; organic acid salts, e.g., palladium acetate, palladium nitrate, palladium oxide, or the like, etc. Other suitable palladium compounds include sodium palladium chloride, palladium amine complex, palladium acetylacetonate, or the like. The content of palladium on the carrier can be selected from a broad range, and is preferably 0.1 – 20% by weight. However, the reaction can be carried out even though the content of palladium is less than 0.1% by weight or more than 20% by weight.

The second component of the catalyst is antimonyl which exists substantially as the oxide thereof. Antimony compounds suitable for the preparation of the catalyst include the halides, e.g., antimony chloride, antimony oxide, antimony sulfate, or the like. The content of antimony on the carrier is not critical and can be selected from a broad range. Good results are obtained with more than 0.05 gram-atoms, preferably 0.05 – 8 gram-atoms, especially 0.5–8 gram-atoms to 1 gram-atom of palladium in the catalyst.

The third component of the catalyst is a carboxylic acid salt of at least one metal selected from alkali metals, alkaline earth metals, zinc, cadmium or lead. Preferred are the aliphatic carboxylic acid salts, e.g., formate, acetate or propionate. It is especially preferable to employ a carboxylic acid salt of the carboxylic acid used as a reactant in the preparation. The content of the carboxylic acid salt on the carrier can be selected from 0.1 – 8 moles, preferably 0.5 – 4 moles to 1 gram-atom of palladium. There is no limitation on the manner of preparation of the catalyst of this invention. Various known methods for preparing supported catalysts can be employed for the preparation of the catalysts of this invention. For example, in order to support the palladium and antimony components on a carrier, the following methods can be employed: The above-mentioned palladium and antimony compounds are dissolved in a suitable solvent. The carrier is dipped in the solution and the solvent is stripped off, whereby the palladium compound and the antimony compound adhere to the carrier. The antimony compounds on the carrier can be converted to the oxide or hydroxide by contacting the same with a basic, neutral or weak acidic aqueous solution, optionally with heating. Alternatively, the carrier can be dipped into a solution of the palladium and antimony compounds and then a precipitant such as an alkali is added to the solution to precipitate the palladium component and the antimony component as hydroxides, oxides, etc., onto the carrier. In either case, the palladium component and the antimony component can be supported on the carrier simultaneously or separately.

The reduction of the palladium component can be carried out either in the presence or absence of the antimony component. Only the palladium component, but not the antimony component, is reduced to the metal form. The reduction can be carried out by conventional reducing methods such as reduction by hydrogen gas or a gaseous organic reducing agent, e.g., methanol, ethylene, propylene; reduction by a conventional reducing agent, e.g., hydrazine, formaldehyde, etc.; or reduction by treatment with a gas containing the aromatic compound having a methyl group which is used as the starting material. The resulting carrier supporting the palladium metal and the antimony component can be dipped into an aqueous solution of the carboxylic acid salt of at least one metal selected from alkali metals, alkaline earth metals, zinc, cadmium or lead so as to support the third component. It is also possible to use a catalyst prepared by supporting the palladium component, an oxide or hydroxide of antimony, and an oxide or hydroxide of at least one metal selected from alkali metals, alkaline earth metals, zinc, cadmium or lead on a carrier by conventional methods. The composite is then contacted with the starting material gas containing the benzene compound selected from toluene or xylene, the aliphatic carboxylic acid, and molecular oxygen. The oxide or hydroxide of said metal is converted by the aliphatic carboxylic acid to the corresponding carboxylic acid salt, and the palladium component is reduced by the benzene compound to the metal, whereas the oxide or hydroxide (hydrated oxide) of antimony remains in the form of oxide.

The starting materials for the process of the invention are the aromatic compounds having a methyl group on the ring, an aliphatic carboxylic acid, and molecular oxygen. Suitable aromatic compounds having a methyl group on the ring include benzene derivatives such as toluene, o-, p-, m-xylene and polycyclic aromatic compounds having a methyl group on the ring such as methyl naphthylene, etc. The aromatic compounds having a methyl group on the ring can also contain a hydroxyl group, an alkoxy group, a carboxyl group or an alkyl group having two or more carbon atoms which is inert to the reaction.

The choice of aliphatic carboxylic acid depends upon the particular desired end product. For industrial processes, it is advantageous to use a lower alkyl carboxylic acid, such as acetic acid, propionic acid, butyric acid, etc., especially acetic acid.

When toluene or xylene and acetic acid are used as the starting materials, the reactions are carried out as follows:

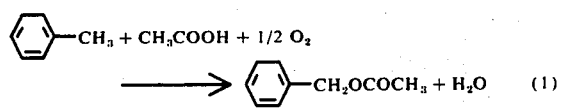

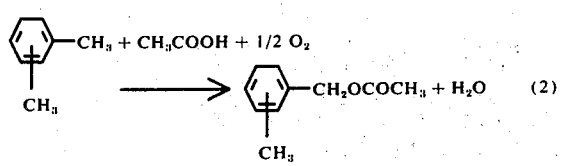

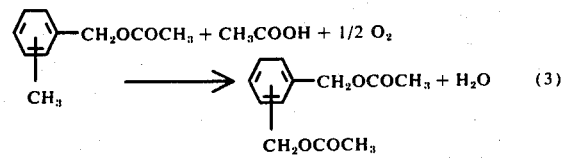

The reaction is normally carried out in the gaseous phase. The reaction can also be performed in the liquid phase. However, in this case, the catalytic component consisting of the carboxylic acid salt of at least one metal selected from alkali metals, alkaline earth metals, zinc, cadmium or lead can be eluted into the liquid phase because the carboxylic acid is present as the medium in the reaction system. The reaction can be performed in any suitable system such as a fixed bed system, a fluidized bed system, etc. It is especially preferable to use a fixed bed multi-pipe type reactor from the viewpoint of efficient heat-removal due to the highly exothermic reaction.

Suitable sources of molecular oxygen used for the reaction include pure oxygen as well as oxygen diluted with an inert gas such as air. The amount of oxygen is not crucial but is usually out of the range of explosion. It is preferred in a concentration of 1 – 50 mole percent of the total gaseous components.

The reaction can be performed under a pressure varying from atmospheric pressure to several tens of atmospheres. It is possible to perform the reaction under higher pressures, or, if desirable, lower pressures.

The reaction temperature should be higher than the temperature required for maintaining the reaction system in the gaseous phase. This temperature is dependent upon the boiling point of the starting materials, the reaction pressure and the ratio of the starting materials. It is usually higher than 130° C. In consideration of the reaction velocity and avoidance of side reactions, the optimum reaction temperature is in the range of 150 ° – 250°C.

The ratio of the aromatic compound having a methyl group on the ring to the aliphatic carboxylic acid can be selected from a broad range. From the viewpoint of catalytic life, it is usually preferred to operate with an amount of carboxylic acid in excess of the equivalent concentration required. The optimum molar ratio of the aromatic compound having a methyl group on the ring to the aliphatic carboxylic acid is 1:1–10.

As stated above, in accordance with this invention, catalytic activity and selectivity of the object product are substantially improved. Additionally, catalytic life is prolonged compared to the lifetime of conventional catalysts. Because of these improvements, the process of the invention is significantly advantageous in industrial production.

Having generally described the invention, a further understanding can be attained by reference to certain specific Examples which are provided herein for purposes of illustration only and are not intended to be limiting in any manner, unless otherwise specified.

EXAMPLE 1

A 50 ml sample of silica (16–30 mesh) was dipped in 50 ml of aqua regia (3 parts by volume of conc. HCl and 1 part by volume of conc. $HNO_3$) containing 4.58 mmole of palladium chloride and 16.00 mmole of antimony chloride. The mixture was gradually concentrated and dried by a rotary evaporator. The resulting solid product was added to a 15% hydrazine aqueous solution and was heated at 40° C for 8 hours to reduce the reducible components. The supernatant solution was removed by a decantation method. The solid product was washed with distilled water. An aqueous solution of zinc acetate of 7.47 mmole dissolved in 75 ml of hot water was added to the solid product and the mixture was gradually concentrated and dried by a rotary evaporator. The resulting catalyst contained 2% by weight of palladium metal, 8% by weight of antimony oxide (calculated as its metal form) and 2% by weight of zinc acetate. A 10 ml sample of the catalyst was placed into a reaction tube made of glass having an inner diameter of 20 mm. A gaseous mixture of glacial acetic acid (560 mmole/hr.) toluene (90 mmole/hr.) and oxygen (40 mmole/hr.) was passed through the reaction tube causing continuous reaction at 220° C. The amounts of the products per 1 gram atom of Pd of the catalyst formed during each 1 hour after the initial 2 hours of the reaction (mole/g-atom Pd.hr.) were calculated and are shown in Table 1. (In Examples 2 – 15 and References 1 – 4, the same calculation unit is used.)

(REFERENCE 1)

The process of Example 1 was repeated escept for use of a catalyst prepared without adding antimony chloride. The results are shown in Table 1.

EXAMPLE 2

The process of Example 1 was repeated for use of a catalyst prepared by adding 2.71 mmole of potassium acetate instead of zinc acetate. The results are shown in Table 1.

EXAMPLE 3

The process of Example 1 was repeated except for use of a catalyst prepared by adding 2.35 mmole of lead acetate instead of zinc acetate. The results are shown in Table 1.

EXAMPLE 4

The process of Example 1 was repeated except reacting at 170° C. The results are shown in Table 1.

(REFERENCE 2)

The process of Example 1 was repeated except for use of a catalyst prepared without adding zinc acetate. The results are shown in Table 1.

EXAMPLES 5 – 6

The process of Example 1 was repeated except for use of catalysts prepared by adding 3.74 mmole (Example 5) or 29.92 mmole (Example6) of zinc acetate. The results are shown in Table 1.

EXAMPLE 7

A 10 ml sample of the catalyst prepared by the process of Example 1 was placed into the reaction tube. A gaseous mixture of water (222 mmole/hr.). toluene (81 mmole/hr.), acetate acid (504 mmole/hr.), and oxygen (40 mmole/hr.) was passed through the reaction tube in accordance with the process of Example 1. The results are shown in Table 1.

EXAMPLE 8

A catalyst was prepared by the process of Example 1 except for use of 50 ml of diatomaceous earth (16–30 mesh) as a carrier and 4.73 mmole of palladium chloride, 16.54 mmole of antimony chloride and 7.72 mmole of zinc acetate. The process of Example 1 was repeated except for use of 10 ml of the catalyst. The results are shown in Table 1.

EXAMPLES 9 – 12

The process of Example 1 was repeated except for use of catalysts prepared by adding antimony chloride in the amounts of 1.00, 4.00, 8.00 and 32.0 mmole, respectively. The results are shown in Table 1.

EXAMPLE 13

A 50 ml sample of silica (30–60 mesh) was dipped in 50 ml of aqua regia containing 5.67 mmole of palladium chloride and 17.48 mmole of antimony chloride. The mixture was gradually concentrated and dried by a rotary evaporator. The resulting solid product was dried by passing nitrogen gas at 150° C for 2 hours. Hydrogen gas was passed at 400° C for 1 hour to reduce the reducible components. An aqueous solution of 8.16 mmole of zinc acetate dissolved in 80 ml of hot water was added to the solid product and the mixture was gradually concentrated and dried by a rotary evaporator. A 10 ml sample of the catalyst was placed into the reaction tube and the process of Example 1 was repeated. The results are shown in Table 1.

EXAMPLE 14

The process of Example 1 was repeated except for use of p-xylene instead of toluene. The results are shown in Table 2.

(REFERENCE 3)

The process of Reference 1 was repeated except for use of p-xylene instead of toluene. The results are shown in Table 2.

EXAMPLE 15

The process of Example 2 was repeated except for use of p-xylene instead of toluene. The results are shown in Table 2.

(REFERENCE 4)

The process of Reference 2 was repeated except for use of p-xylene instead of toluene. The results are shown in Table 2.

EXAMPLE 16

An aqueous solution prepared by dissolving 12.5 g of antimony chloride in a mixture of 3 ml of conc. HCl and 10 ml of distilled water was admixed at room temperature with an aqueous solution prepared by dissolving 13.4 g of zinc chloride in a mixture of 1 ml of conc. HCl and 10 ml of distilled water. One-third of the volume of the resulting solution was mixed with 50 ml of silica (manufactured by Nikki Kagaku Kabushiki Kaisha N608), and the mixture was allowed to stand for 1 hour. An aqueous solution prepared by dissolving 12 g of ammonium sulfate in 33 ml of distilled water was added to the product and the mixture was heated for 1 hour in a hot water bath. After cooling, it was neutralized with 28% ammonia water to adjust the pH to 7. It was then heated for 1 hour. The solid product was washed with distilled water and dried by a rotary evaporator. It was subsequently calcined at 400° C for 3 hours in air to produce a white solid product. The white solid product was dipped into an aqueous solution prepared by dissolving 0.886 g of palladium chloride in 1 ml of conc. HCl under heating, diluting with 150 ml of water and adjusting the pH to 4.0 by adding sodium carbonate. The mixture was concentrated and dried by a rotary evaporator. The resulting catalyst contained 2% by weight of $Pd^{2+}$, 8% by weight of $Sb^{3+}$ and 4.3% by weight of $Zn^{2+}$ relative to the weight of the carrier, were $Pd^{2+}$ is in the form of hydroxide, $Sb^{3+}$ is in the form of hydrated oxide, and $Zn^{2+}$ is in the form of hydroxide. The process of Example 1 was repeated except for the use of 10 ml of the catalyst. In the course of reaction, $Pd^{2+}$ was reduced by toluene to the metal and $Zn^{2+}$ was converted by acetic acid to the acetate, whereas $Sb^{3+}$ remained in the form of oxide. The amount of benzyl acetate per 1 gram-atom of palladium contained in the catalyst (mole/g-atom Pd. hr.) formed during each 1 hour after the initial 10, 25, and 46 hours of the reaction were calculated and are shown in Table 1.

What is claimed as new and intended to be covered by Letters Patent is:

1. In a process for preparing a carboxylic ester of a substituted benzene compound having one or two hydroxymethyl groups on the benzene ring by reacting a benzene compound selected from the group consisting of toluene and xylene, a lower alkanoic acid, and molecular oxygen in the gaseous phase in the presence of a catalyst, the improvement which comprises:
   reacting said reactants over a supported catalyst wherein the active constituents consist essentially of:
   a. palladium metal,
   2. and antimony component substantially as the oxide thereof, and
   3. at least one carboxylic acid salt of an alkali metal, an alkaline earth metal, zinc, cadmium or lead or a carrier.

2. The process of claim 1, wherein the content of palladium in the catalyst is 0.1 – 20% by weight of the total weight of the catalyst.

3. The process of claim 1, wherein the content of antimony is 0.05 – 8 gram-atom to 1 gram-atom of palladium in the catalyst.

4. The process of claim 1, wherein the content of antimony is 0.5 – 8 gram-atom to 1 gram-atom of palladium in the catalyst.

5. The process of claim 1, wherein the carboxylic acid salt is a salt of a metal selected from the group consisting of alkali, alkaline earth, zinc, cadmium and lead, and the anion is selected from the group consisting of formate, acetate and propionate.

Table 1

| | | Catalyst components | | | | Products (mole/g-atom Pd.hr.) | | |
|---|---|---|---|---|---|---|---|---|
| | Pd wt. % | Sb(oxide) wt. %(as metal) | carboxylate type[1] | wt. % | Reaction temp. °C | $CH_2OCOCH_3$ (Ph) | CHO (Ph) | $CH_3$ (Ph)–$OCOCH_3$ [2] |
| Example 1 | 2.0 | 8.0 | $Zn(OAc)_2$ | 2.0 | 220 | 6.40 | 0.28 | 0.08 |
| Reference 1 | " | 0 | " | " | " | 0.81 | 0.30 | trace |
| Example 2 | " | 8.0 | KOAc | " | " | 8.09 | 0.43 | 0.11 |
| " 3 | " | " | $Pb(OAc)_2$ | " | " | 3.42 | 0.68 | trace |
| " 4 | " | " | $Zn(OAc)_2$ | " | 170 | 3.41 | 0.41 | " |
| Reference 2 | " | " | — | — | 220 | 0.36 | 0.03 | " |
| Example 5 | " | " | $Zn(OAc)_2$ | 1.0 | " | 7.67 | 0.21 | " |
| " 6 | " | " | " | 8.0 | " | 7.41 | 0.58 | 0.08 |
| " 7 | " | " | " | 2.0 | " | 9.37 | 0.39 | 0.10 |
| " 8 | " | " | " | " | " | 8.88 | 0.57 | trace |
| " 9 | " | 0.5 | " | " | " | 1.24 | 0.25 | " |
| " 10 | " | 2.0 | " | " | " | 5.01 | 0.22 | 0.06 |
| " 11 | " | 4.0 | " | " | " | 7.80 | 0.51 | 0.15 |
| " 12 | " | 16.0 | " | " | " | 3.34 | 0.33 | 0.04 |
| " 13 | " | 8.0 | " | " | " | 9.01 | 0.85 | 0.20 |
| " 16 | " | " | " | 12 | " | 7.62[3] 8.80[4] 9.60[5] | | |

[1]—Ac = —$COCH_3$
[2]total of o-, m- and p-compounds
[3]10 hours after initiation
[4]25 hours after initiation
[5]46 hours after initiation Table 2

| | Catalyst components | | | | | Products (mole/g-atom Pd. hr.) | | | |
|---|---|---|---|---|---|---|---|---|---|
| | Pd wt. % | Sb(oxide) wt. % (as metal) | carboxylate type | wt. % | Reaction temp. °C | CHO (Ph)–$CH_3$ | $CH_2OCOCH_3$ (Ph)–$CH_3$ | $CH(OCOCH_3)_2$ (Ph)–$CH_3$ | $CH_2OCOCH_3$ (Ph)–$CH_2OCOCH_3$ |
| Example 14 | 2.0 | 8.0 | $Zn(OCOCH_3)_2$ | 2.0 | 220 | 0.18 | 1.74 | 0.26 | 0.77 |
| Example 15 | " | " | $KOCOCH_3$ | " | " | 0.35 | 2.50 | 0.19 | 1.40 |
| Reference 3 | " | 0 | $Zn(OCOCH_3)_2$ | " | " | trace | 0.17 | trace | 0.07 |
| Reference 4 | " | 8.0 | — | — | " | trace | 0.52 | trade | 0.10 |

Having now fully described the invention, it will be apparent to one of ordinary skill in the art that many changes and modifications can be made thereto without departing from the spirit or scope of the invention as set forth herein.

6. The process of claim 5, wherein the anion of the carboxylic acid salt is the same as the carboxylic acid used as the starting material.

7. The process of claim 5, wherein said carboxylic acid salt is present in an amount of 0.1 – 8 moles to 1 gram-atom of palladium.

8. The process of claim 7, wherein said carboxylic acid salt is present in an amount of 0.5 – 4 moles to 1 gram-atom of palladium in the catalyst.

9. The process of claim 1, wherein said benzene compound is toluene.

10. The process of claim 1, wherein said benzene compound is xylene.

11. The process of claim 1, wherein the carboxylic acid is acetic acid.

12. The process of claim 1, wherein the molar ratio of said benzene compound to the carboxylic acid is 1 :1 – 10.

13. The process of claim 1, wherein the reaction is carried out at 150°–250° C.

14. The process of claim 1, wherein the amount of oxygen is 1 – 50 mole percent of the total gaseous components.

* * * * *